United States Patent [19]
Nall

[11] Patent Number: 5,410,091
[45] Date of Patent: Apr. 25, 1995

[54] RHODIUM CATALYZED OXO PROCESS IN TUBULAR REACTOR

[75] Inventor: Charles S. Nall, Dothan, Ala.

[73] Assignee: Quimica Oxal C.A., Caracas, Venezuela

[21] Appl. No.: 252,737

[22] Filed: Jun. 2, 1994

[51] Int. Cl.⁶ .............................................. C07C 45/50
[52] U.S. Cl. .................... 568/454; 568/451; 568/452; 568/453
[58] Field of Search ................ 568/451, 453, 454, 452

[56] References Cited

U.S. PATENT DOCUMENTS

| | | | |
|---|---|---|---|
| 2,504,682 | 4/1950 | Harlan | 568/451 |
| 2,571,160 | 10/1951 | Parker et al. | 568/451 |
| 2,664,433 | 12/1953 | Hudson | 568/451 |
| 2,757,202 | 7/1956 | Mertzweiller et al. | 568/451 |
| 2,827,491 | 3/1958 | Mertzweiller | 568/451 |
| 2,880,241 | 3/1959 | Hughes | 568/451 |
| 3,113,974 | 6/1959 | Heimsch et al. | 568/451 |
| 3,239,566 | 3/1966 | Slaugh et al. | 568/454 |
| 3,271,458 | 9/1966 | Ellis et al. | 568/451 |
| 3,518,319 | 6/1970 | Ellert et al. | 568/451 |
| 3,527,809 | 9/1970 | Pruett et al. | 568/454 |
| 3,868,422 | 2/1975 | Hart et al. | 568/454 |
| 3,929,900 | 12/1975 | Schnur et al. | 568/454 |
| 4,210,426 | 7/1980 | Sridhar | 55/68 |
| 4,593,127 | 6/1986 | Bunning et al. | 568/454 |
| 4,613,701 | 9/1986 | Strong | 568/454 |
| 5,001,274 | 3/1991 | Bunning | 568/454 |
| 5,087,763 | 2/1992 | Sorensen | 568/492 |
| 5,105,018 | 4/1992 | Miyazawa et al. | 568/453 |
| 5,110,990 | 5/1992 | Blessing et al. | 568/492 |

Primary Examiner—Werren B. Lone
Attorney, Agent, or Firm—Brooks & Kushman

[57] ABSTRACT

An improved process for the hydroformylation of olefins with carbon monoxide and hydrogen in the presence of a hydroformylation catalyst in a continuous tubular reactor, the improvement comprising:
  a. employing an rhodium hydroformylation catalyst;
  b. maintaining the reaction temperature at less than about 145° C.; and
  c. maintaining the pressure at less than 450 psig and the partial pressure therein attributable to carbon monoxide no greater than about 90% of the total pressure;
whereby the hydroformylated olefin product is rich in normal aldehydes.

29 Claims, 2 Drawing Sheets

RHODIUM CATALYZED OXO PROCESS IN TUBULAR REACTOR

TECHNICAL FIELD

This invention relates to an improved process for the preparation of organic oxygenated compounds containing a high ratio of normal aldehydes to branched-chain aldehydes which comprises reacting certain olefinic compounds with carbon monoxide and hydrogen under a specific combination of carefully controlled reaction conditions in the presence of certain rhodium-containing complex catalysts and tertiary organo-containing ligands described hereinafter.

BACKGROUND ART

Processes directed to the production of reaction mixtures comprising substantial amounts of aldehydes and at times lesser amounts of alcohols by the reaction of olefinic compounds with carbon monoxide and hydrogen at elevated temperatures and pressures in the presence of certain catalysts are well known in the art. The aldehydes and alcohols produced generally correspond to the compounds obtained by the addition of a carbonyl or carbinol group to an olefinically unsaturated carbon atom in the starting material with simultaneous saturation of the olefin bond. Isomerization of the olefin bond may take place to varying degrees under certain conditions with the consequent variation in the products obtained. Such processes are generally known in the industry under varying names such as the oxo process or reaction, oxonation and/or hydroformylation.

One disadvantage of prior art hydroformylation processes is their dependence upon the use of catalysts such as cobalt octacarbonyl which require exceptionally high operative pressures to maintain such catalysts in their stable form. Another disadvantage is the difficulty in obtaining hydroformylation products which have a relatively high normal to branched-chain isomer ratio.

U.S. Pat. No. 2,880,241 (Hughes) discloses that rhodium-containing catalysts are effective for oxygenating olefins, thereby permitting a "more selective and a different kind of carbonylation." The patentee states that normally, the cobalt catalyzed oxo reaction produces a mixture of two or more isomers "whereas rhodium catalyzed carbonylation at low temperatures, such as 60°–120° C., permits the production of predominantly (75% to 90%) branched isomer" (see column 1, lines 44–57 of U.S. Pat. No. 2,880,241).

U.S. Pat. No. 3,239,566 (Slaugh et al) discloses that complexes of rhodium and phosphines catalyze the oxo reaction to give oxygenated products predominating in aldehydes and/or alcohols. Slaugh et al prefer to employ trialkylphosphine-rhodium-carbonyl complex catalysts at a temperature of from about 150° C. to about 210° C.. The patentees' examples disclose that their rhodium-containing catalyzed process results in oxygenated products having an isomer distribution of normal aldehydes to branched-chain aldehydes which is comparable to cobalt-containing catalyzed oxo processes.

U.S. Pat. No. 3,527,809 (Pruett et al), the entire contents and disclosure of which is incorporated herein by reference, discloses an oxo process for preparing oxygenated or oxonated products containing a high ratio of normal to branched-chain aldehydes by reacting olefins with carbon monoxide and hydrogen in the presence of certain rhodium hydroformylation catalysts.

Tubular reactors have been employed in carrying out the oxo process; however, it has been reported that the use of such tubular reactors enhances the production of alcohols at the expense of aldehydes. Moreover, the tubular reactors have been employed in conjunction with cobalt catalysts and the employment of high temperatures and pressures. See U.S. Pat. No. 3,113,974 (Heimsch et al).

It is an object of the present invention to provide an improved oxo process for the hydroformylation of olefins with carbon monoxide and hydrogen utilizing rhodium catalysts and mild reaction conditions in a tubular reactor, whereby not only is the predominant product an aldehyde, but the ratio of normal to branched-chain aldehydes is enhanced, a result heretofore believed to be unachievable using a tubular reactor.

SUMMARY OF THE INVENTION

These and other objects are realized by the present invention which provides an improved process for the hydroformylation of olefins with carbon monoxide and hydrogen in the presence of a hydroformylation catalyst in a continuous tubular reactor, the improvement comprising:

a. employing an olefin hydroformylation catalytically effective amount of a rhodium hydroformylation catalyst;

b. maintaining the reaction temperature in the tubular reactor at less than about 145° C.; and c. maintaining the pressure within the tubular reactor at less than 450 psig and the partial pressure therein attributable to carbon monoxide no greater than about 90% of the total pressure;

whereby the hydroformylated olefin product is rich in normal aldehydes.

In a further embodiment of the invention, the olefins are partially hydroformylated with carbon monoxide and hydrogen in the presence of a rhodium hydroformylation catalyst in at least one pot reactor prior to completion of hydroformylation in a tubular reactor as described above.

BEST MODE FOR CARRYING OUT THE INVENTION

The present invention is predicated on the discovery that the conventional rhodium catalyzed oxo process, which is traditionally a low pressure, low temperature method requiring certain well defined ratios of carbon monoxide to hydrogen in the synthesis gas, may be carried out in conventional tubular reactors which typically employ cobalt catalysts and relatively rigorous conditions resulting in the production of high levels of alcohols at the expense of aldehydes, to produce a product rich in normal aldehydes, i.e., a n/i ratio of at least 6:1 or greater, and preferably about 10:1.

The advantages produced by the claimed improved method are that the high efficiency and mass transfer characteristics inherent in the tubular reaction system surprisingly obtained in a low temperature, low pressure oxo process catalyzed by rhodium as opposed to cobalt, to produce an oxonated product low in alcohol content and having a high normal- to iso-aldehyde ratio.

The chemistry of the improved process, i.e., the reaction conditions, reactants, catalysts, reaction parameters, etc., are virtually identical to that disclosed in U.S. Pat. No. 3,527,809 (Pruett et al., supra) to which reference may be had for a description thereof.

That patent describes a novel process for preparing oxygenated products comprising aldehydes which have high normal to iso- or branched-chain isomer ratios. Such process involves using a certain class of rhodium-containing complexes to effectively catalyze, in the presence of tertiary organo-containing ligands, the oxo reaction whereby certain olefinic compounds are reacted with hydrogen and carbon monoxide under a specific combination of conditions. In accordance with the invention, the process variables which fall within critically specified limits are the (1) rhodium-containing complex catalyst, (2) olefinic feed, (3) tertiary organo-containing ligand and its concentration, (4) temperature range, (5) total gas pressure, and (6) the partial pressures exerted by hydrogen and carbon monoxide. By practice of the novel process, the inventor was able to obtain oxygenated products in which the aldehydes thereof are highly enriched in the normal straight-chain form, that is, isomer ratios of normal to branched-chain aldehydes as high as about 30:1 and higher at respectable conversions have been obtained by the practice of the patented process.

The catalysts which are contemplated consist essentially of rhodium in complex combination with carbon monoxide and a ligand containing a trivalent atom of a Group VA element including phosphorous, arsenic and antimony, said trivalent atom possessing one available pair of electrons. The ligand can be a tertiary organo phosphorous compound, a tertiary organo arsenic compound or a tertiary organo antimony compound, and desirably wherein each organo moiety is composed of (1) carbon and hydrogen atoms, or (2) carbon, hydrogen and aliphatic etheric oxygen atoms, each of the organo moieties being monovalently bonded to the trivalent Group VA element through a carbon atom or an aliphatic etheric oxygen atom thereof. The organo moieties can also contain other substituents such as cyano and halo, e.g., chloro. The term "aliphatic etheric oxygen atom" is meant to convey the —O— group which does not form part of a heterocyclic ring such as, for example, dioxane. Consequently, the —O— groups present in, for instance, the trialkylphosphites or the triarylphosphites are considered, for purposes of this definition, to be "aliphatic etheric oxygen atoms." Strictly speaking, though, the oxygen atom in the trialkylphosphites and the triarylphosphites stem from the corresponding acid, i.e., phosphorous acid. As such, various authorities consider the phosphite compounds to be esters. In its active form, the suitable complex catalysts will contain the rhodium component in a reduced valence state. This will normally be a zero valence state and may suitably be even lower, such as a minus one (−1) valence state. The term "complex" as used herein (including the claims) means a coordination compound formed by the union of one or more electronically rich molecules or atoms capable of independent existence with one or more electronically poor molecules or atoms, each of which is also capable of independent existence. The suitable ligands, as indicated above, possess an element, i.e., phosphorous, arsenic or antimony, which has one available or unshared pair of electrons. When such elements have this electronic configuration, they are capable of forming a coordinate bond with rhodium.

It is preferred that the aforesaid ligands possess a AHNP value of at least about 425, and more preferably at least about 500. By "ΔHNP" is meant the difference in the half-neutralization potential between the ligand under consideration and N,N'-diphenylguanidine as determined according to the procedure set out in the article by C. A. Streuli, ANALYTICAL CHEMISTRY, Vol. 32, pp. 985–987 (1960). The AHNP value is a measure of the basicity of the ligand. For example, the relatively strong basic phosphorous-containing ligands such as those possessing a AHNP value substantially below 425 gave complexes that were ineffective in the practice of the process as evidenced by a lack of a discernible reaction rate and/or low normal to branched-chained aldehydic product isomer ratios. Those phosphorous-containing ligands which possessed a ΔHNP value of at least about 425, and preferably at least about 500, are relatively less basic compounds. Complex catalysts prepared from such ligands effectively catalyzed the process, whereby a product mixture resulted which contained a high normal to branched-chained aldehyde isomer ratio.

In Table 1 below, the ΔHNP values of several illustrative phosphorous-containing ligands are set out.

TABLE 1

| LIGANDS | ΔHNP* |
|---|---|
| $P(CH_3)_3$ | 114 |
| $P(C_2H_5)_3$ | 111 |
| $P(n-C_3H_7)_3$ | 115 |
| $P(n-C_4H_9)_3$ | 131 |
| $P(iso-C_4H_9)_3$ | 167 |
| $P(n-C_5H_9)_3$ | 139 |
| $P(2-n-C_4H_9OC_2H_4)_3$ | 162 |
| $P(2-C_6H_5C_2H_4)_3$ | 273 |
| $P(C_6H_{11})_3$ | 33 |
| $P(CH_3)(C_2H_5)_2$ | 117 |
| $P(CH_3)_2(C_2H_5)$ | 117 |
| $P(CH_3)_2(C_6H_5)$ | 281 |
| $P(C_2H_5)_2(C_6H_5)$ | 300 |
| $P(C_6H_{11})_2(2-CNC_2H_4)$ | 232 |
| $P(CH_3)_2(2-CNC_2H_4)$ | 291 |
| $P(n-C_4H_9)_2(2-CNC_2H_4)$ | 282 |
| $P(n-C_8H_{17})_2(2-CNC_2H_4)$ | 297 |
| $P(p-CH_3OC_6H_4)_3$ | 439 |
| $P(C_6H_5)_3$ | 573 |
| $P(C_6H_5)_2(C_2H_5)$ | 400 |
| $P(C_6H_5)_2(n-C_4H_9)$ | 400 |
| $P(O-n-C_4H_9)_3$ | 520 |
| $P(OCH_3)_3$ | 520 |
| $P(OC_6H_5)$ | 875 |

*E. M. Thorsteinson et al., JOUR. AM. CHEM. SOC., Vol. 88, pp. 3929–3936 (1966); and C. A. Streuli, ANALYTICAL CHEMISTRY, Vol. 32, pp. 985–987 (1960).

Aside from possible exceptions, it is apparent from a consideration of Table 1 above that tertiary organo phosphorous-containing ligands in which at least two of the organo moieties are alkyl and/or cycloalkyl groups are excluded from the scope of the method. Classes of ligands which are excluded, therefore, are the trialkylphosphines, the tricycloalkylphosphines, the mixed (alkyl)(cycloalkyl)phosphines, the dialkylarylphosphines, the diarylalkylphosphines and the dicycloalkylarylphosphines.

By way of illustration, suitable classes of triorganocontaining ligands which are contemplated in the practice of the method include the trialkylphosphites, the tricycloalkylphosphites, the trialkylphosphines, the triarylphosphines, the triarylstibines and the triarylarsines. Desirably, each organo moiety in the ligand does not exceed 18 carbon atoms. The triarylphosphites and the triarylphosphines represent the preferred classes of ligands. Specific examples of ligands which are suitable in forming the complex catalysts include trimethylphosphite, triethylphosphite, butyldiethylphosphite, tri-n-propylphosphite, tri-n-butylphosphite, tri-2-ethylhexylphosphite, tri-n-octylphosphite, tri-n-dodecylphosphite, triphenylphosphite, trinaphthylphosphite, triphenylphosphine, tri(p-chlorophenyl)phosphite, trinaphthylphosphine, phenyl diphenylphosphinite, diphenyl phenylphosphonite, diphenyl ethylphosphonite, triphenylarsine, triphenylstibine, tris(p-chloro-phenyl)phosphine, tri(p-cyanophenyl)phosphite, tri(p-methoxyphenyl)phosphite, ethyl diphenylphosphinite and the like. Triphenylphosphite and triphenylphosphine are examples of the most preferred ligands. Such preferred ligands resulted in complex catalysts which effectively catalyzed alpha-olefinic compounds at highly satisfactory reaction rates and also yielded high normal to branched-chain aldehydic product isomer ratios.

For the sake of convenience and brevity, and primarily since the tertiary organo phosphorous compounds are the ligands of choice, the method shall oftentimes be exemplified by continually referring to such phosphorous-containing compounds. As previously indicated, the trivalent phosphorous-containing ligand should have a ΔHNP value of at least about 425. Moreover, these ligands should be free of interfering or so-called sterically hindered groups. Ligands such as the triarylphosphines and the triarylphosphites which are characterized by the presence of "bulky" groups, e.g., phenyl, tolyl, etc., in the ortho position of the aryl moieties have been observed to give catalyst complexes which are unsuitable.

The process contemplates alpha-olefinic compounds as reactants in the process. Such alpha-olefinic compounds are characterized by a terminal ethylenic carbon-to-carbon bond which may be a vinylidene group, i.e., or a vinyl group, i.e., They may be straight-chain or branched-chain and may contain groups or substituents which do not essentially interfere with the course of the process. Such groups or substituents may be illustrated by carbonyl:

oxy (—O—), hydroxy (—OH), carboxy (—COOH), halo, alkoxy, phenyl, haloalkyl, etc. The alpha-olefinic compounds may contain one ethylenic bond or it may contain more than one ethylenic bond.

Illustrative alpha-olefinic compounds which may be employed as reactants include propylene, 1-butene, 1-pentene, 1-hexene, 1-heptene, 1-octene, 1-decene, 1-dodecene, 1-octadecene, 2-ethyl-1-hexene, styrene, 3-phenyl-1-propene, allyl chloride, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, vinyl methyl ether, allyl ethyl ether, n-propyl 7-octenoate, 3-butanoic acid, 7-octanoic acid, 3-butenenitrile, 5-hexenamide and the like. Preferred alpha-olefinic compounds include alkenes, alkyl alkenoates, alkenyl alkanoates, alkenyl alkyl ethers and alkenols, especially those which contain up to 20 carbon atoms.

The process is effected in the presence of a catalytically significant quantity of the complex catalyst. The hydroformylation reaction will proceed when employing as little as about $1 \times 10^{-2}$ mol and even lesser amounts of rhodium (from the complex catalyst) per mol of alpha-olefinic feed. However, such catalyst concentrations, though operable, are not particularly desirable since the reaction rate appears to be too slow and thus not commercially attractive. The upper catalyst concentration limit can be as high as about $1 \times 10^{-1}$ mol and higher of rhodium per mol of alpha-olefinic feed. However, the upper limit appears to be dictated and controlled more by economics in view of the high cost of rhodium metal and rhodium compounds. No particular advantages at such relatively high concentrations are manifest. A catalyst concentration of from about $1 \times 10^{-4}$ mol to about $5 \times 10^{-2}$ mol of rhodium metal per mol of alpha-olefinic feed is desirable. A concentration of from about $1 \times 10^{-4}$ to about $1 \times 10^{-2}$ mol of rhodium per mol of alpha-olefin is preferred. Observations generally indicate that optimum results are obtained by employing a catalyst concentration falling within the aforementioned preferred range. It is thus apparent that the concentration of the complex catalyst can vary over a rather wide range.

The concentration of ligand, e.g., the triorgano phosphorous ligand, to rhodium metal, on the other hand, is rather critical. Regardless whether one preforms the active complex catalyst prior to introduction in the hydroformylation reaction zone or whether the active catalyst species is prepared in situ during the hydroformylation reaction, it is essential that the reaction be effected in the presence of free ligand. By "free ligand" is meant the tertiary organo Group VA compounds as exemplified by triphenylphosphite that are not tied to or complexed with the rhodium atom in the active complex catalyst. Though not wishing to be held to any theory or mechanistic discourse, it appears that the active catalyst species contains, in its simplest form, a concentration of triorgano phosphorous ligand and carbon monoxide equal to a total of four mols in complex combination with one mol of rhodium. Thus, the active species may comprise a complex catalyst mixture, in their monomeric forms, which are characterized by one, two and/or three triorgano phosphorous molecules complexed with one molecule of rhodium. As can be surmised from the above discussion, carbon monoxide (which incidentally is also properly classified as a ligand) is likewise present and complexed with the rhodium in the active species. In some instances, the active catalyst species may also contain hydrogen as a ligand. The ultimate composition of the active complex catalyst can be likened or attributable to the outcome of competing reactions between carbon monoxide and the triorgano phosphorous ligand for "complexing sites" with the rhodium element. These competing reactions may be disturbed or influenced, within significant limits, by increasing or decreasing the partial pressure due to carbon monoxide, or by increasing or decreasing the concentration of the triorgano phosphorous ligand. As a generalized statement, therefore, the component (carbon monoxide or triorgano phosphorous ligand) which can shift the equilibrium of the competing reaction in its favor should enjoy the greater opportunities of occupying the "complexing sites" with rhodium to give the active complex catalyst. One could view the function of free triorgano phosphorous ligand as either maintaining the status quo of the various forms of active complex catalyst during the hydroformylation, or as a means for shifting the equilibrium of the competing reactions in its favor and, therefore, causing additional triorgano phosphorous ligands to enter into complex combination with rhodium with the probable eviction of a similar number of carbon monoxide ligands from the complex catalyst. One could postulate that the unexpected and unobvious advantages which accrue from the practice of the invention are due, in part, to a carefully controlled and well defined hydroformylation process in which the complexing affinity between the triorgano phosphorous ligand and rhodium appears to approach the maximum at the expense or minimization of the complexing attraction between the carbon monoxide ligand and rhodium.

In a desirable embodiment, the process is effected by employing a hydroformylation reaction mixture which contains at least about 2 mols of free triorgano phosphorous ligand per mol of rhodium. It is preferred that at least about 5 mols of free triorgano phosphorous ligand per mol of rhodium be employed. The upper limit does not appear to be narrowly critical and its concentration would be dictated largely by commercial and economic considerations. A practical upper limit concerning the molar ratio of triorgano phosphorous ligand to rhodium would be approximately 100:1; an upper limit of about 30:1 is considered, for most instances, to be within the contemplated commercially attractive area.

A unique feature of the invention is the exceptionally low total pressures of hydrogen and carbon monoxide which are required to effect a commercial process. Total pressures of less than about 450 psia and as low as one atmosphere and lower, may be employed with effective results. Total pressures of less than about 350 psia are preferred. A total pressure range of greater than about one atmosphere and less than about 250 psia is highly preferred since the unexpected and unobvious advantages discussed hereinabove are readily attained when conducting the process at such low total pressures. The savings in equipment costs is readily apparent as well.

The partial pressure of the carbon monoxide has been found to be an important factor in the process. It has been observed that a noticeable decrease occurs in the normal/isoaldehyde product isomer ratio as the partial pressure attributable to carbon monoxide approaches a value of about 75% of the total gas pressure ($CO+H_2$). Thus, the partial pressure attributable to carbon monoxide is desirably no greater than about 75% of the total gas pressure ($CO+H_2$). However, in certain instances, it may be plausible to increase the carbon monoxide partial pressure to a value of above about 75% of the total gas pressure, for instance, to about 80% or even 85%, by employing a very large excess of free triorgano phosphorous ligand; however, in such cases, one would be departing somewhat from attaining a truly commercial operation. In general, a partial pressure attributable to hydrogen of from about 25 to 90% based on the total gas pressure ($CO+H_2$) is suitable. It is most advantageous to employ a total gas pressure in which the partial pressure attributable to hydrogen is at least about 50% of the total gas pressure. Outstanding results have been attained when the hydrogen partial pressure represented about 45% to about 75% of the total gas pressure.

Another important variable of the process is the exceptionally low operative temperatures which can be employed in conjunction with the extremely low operative pressures and other well defined variables. The process can be conducted at temperatures as low as about 50° C. and up to 145° C. with advantageous results. A temperature in the range of from about 60° C. to about 125° C. is preferred. Within this preferred range, maximum beneficial results are attained. In many instances, a temperature range of from about 65° C. to 95° C. is suitable and practical, especially from an obvious economic viewpoint.

The concentration of the alpha-olefinic feed is not a critical limitation and may vary over an extremely wide range. For example, one would employ ratios of alpha-olefinic feed to complex catalyst between about 1200:1 and about 1:8; however, it must be understood that such ratios are merely illustrative and higher, as well as lower, ratios are contemplated and are within the scope of the invention.

The residence period can vary from about a couple minutes to several hours in duration and, as is well appreciated, this variable will be influenced, to a certain extent, by the reaction temperature, the choice of the alpha-olefinic reactant, the catalyst, the ligand, the concentration of the ligand, the total synthesis gas pressure and the partial pressure exerted by its components, as well as other factors. As a practical matter, the reaction is effected for a period of time which is sufficient to hydroformylate the alpha or terminal ethylenic bond of the alpha-olefinic reactant.

Solvents are not required in the practice of the invention, but oftentimes their use is desirable and practical. One may employ normally liquid organic solvents which are inert or which do not interfere to any substantial degree with the desired hydroformylation reaction under the operative conditions employed. Illustrative of such solvents include the saturated hydrocarbons such as the pentanes, naphtha, kerosene, mineral oil, cyclohexane, etc., as well as the aromatic hydrocarbons, ethers, ketones and nitriles as illustrated by benzene, xylene, toluene, diethyl ether, acetophenone, cyclohexanone, benzonitrile, and the like.

The preparation of the catalysts employed in the novel hydroformylation reaction is documented in the literature. A suitable method is to combine the rhodium salt of an organic acid with the ligand, e.g., triphenylphosphite, triphenylphosphine, etc., in the liquid phase. The valence state of rhodium may then be reduced by hydrogenating the solution prior to the use of the catalyst therein. Alternatively, the catalysts may be prepared from a carbon monoxide complex of rhodium. For example, one could start with dirhodium octacarbonyl and, by heating this substance with the ligand, the ligand will replace one or more of the carbon monoxide molecules, thus producing the desired catalyst. It is also possible to start with the ligand of choice and rhodium metal, or an oxide of rhodium, and prepare the active catalyst species in situ during the hydroformylation reaction.

Adapting the above-described process to the conventional tubular reactor results in the efficient production of an oxygenated product high in normal aldehyde content at low cost.

Figure 1:
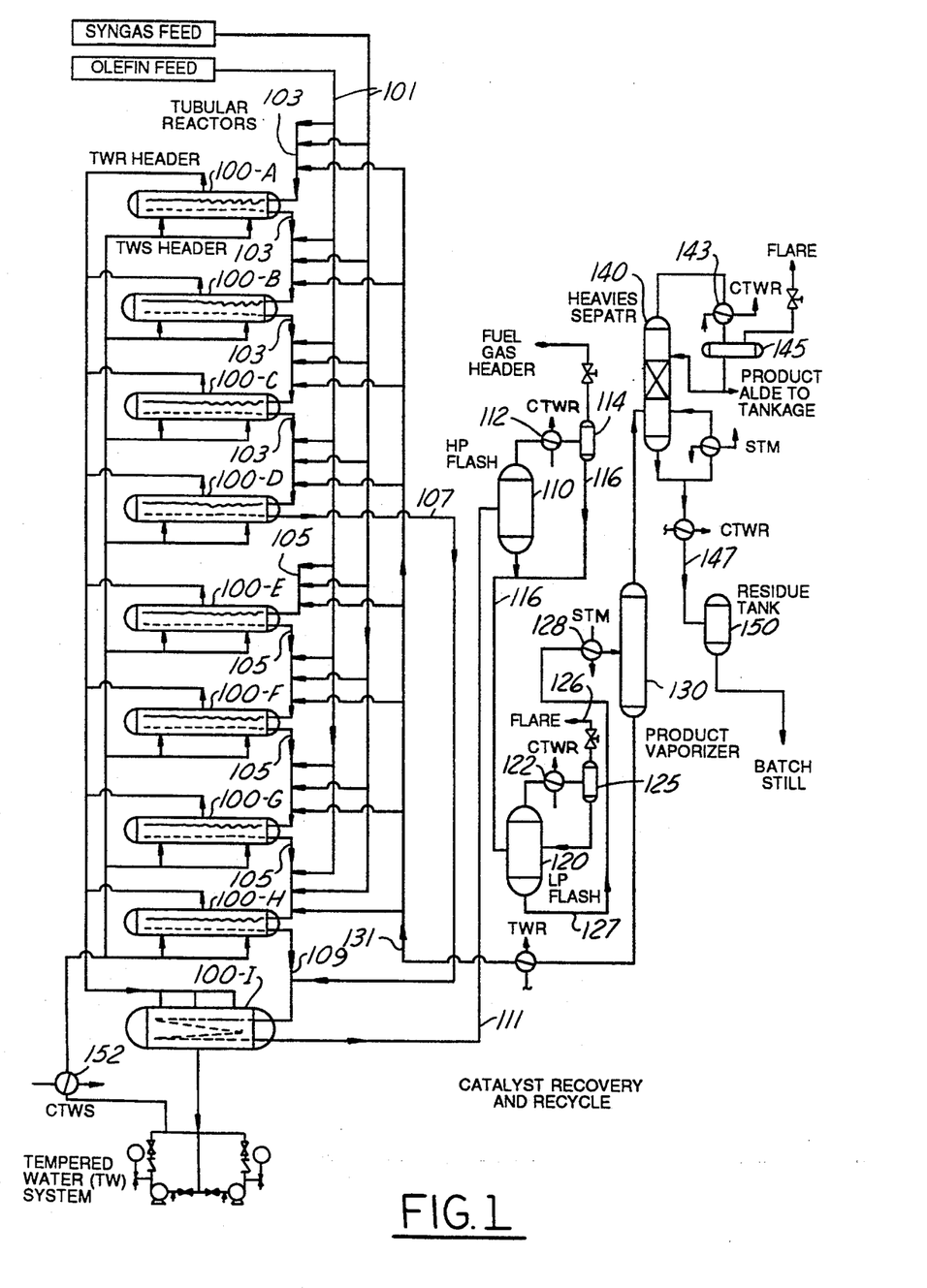
FIG. 1 is a schematic flow diagram of an embodiment of the method of the invention which depicts in detail the tubular reactor portion of the system.

FIG. 1 depicts a system for carrying out the method of the invention which does not employ "Continuous Stirred Tank Reactors" (CSTRs), but which depends solely on the use of "tubular" reactors for carrying out the oxo process. The tubular reactor is indicated generally by 100 and consists of bundles 100-A through 100-I, each containing continuous sections of reactor tubing. The bundles are arranged in two parallel trains, each containing four bundles to minimize pressure drop through the system. The interior diameters of the tubes are such to ensure a well mixed stream of reactants and to maintain turbulent flow.

Synthesis gas (CO+$H_2$) and olefin, i.e., propylene, flow to a manifold 101 in the reactor area where the reactants are controllably fed in a staged manner to successive reactor bundles 100-A through 100-I. Active rhodium catalyst at the desired concentration is cooled and recycled from the product vaporizer 130 to a manifold 131 in the reaction area. The catalyst stream is controllably added to each reactor bundle 100-A through 100-I as required to maintain desired catalyst concentrations and provide the liquid reaction medium required for the liquid phase reaction to occur. The catalyst, propylene and syngas streams are combined and mixed in an in-line static mixer prior to entering each tubular bundle. The mixers enhance dispersion of the vapor feeds into the liquid reaction medium, maximizing interfacial area and reducing mass transfer limitations to the reaction process. The mixer is commercially available (Sulzer Model No. SMV T2) and is inserted into the line.

Product is first formed in reactor bundles 100-A and 100-E, then transferred to successive bundles through interconnecting manifolds 103,105. Syngas, olefin feed and catalyst are controllably added to the inlet (incoming arrow) of each reactor bundle. Manipulation of individual reactor hydrogen, carbon monoxide and propylene partial pressure, as well as reactor temperature and catalyst concentration, allow maximization of olefin conversion and normal/iso product ratio. Final product is conveyed from bundles 100-D and 100-H to bundle 100-I by product transfer lines 107,109, with bundle 100-I functioning as a product cooler.

From bundle 100-I, product is transferred via line 111 to the high pressure (HP) separator 110 where unreacted gases are separated from the liquid product (primarily hydrogen and carbon monoxide). The overhead gases from the HP separator are cooled in exchanger 112, and condensed liquid is separated in tank 114 and sent through line 116 to a low pressure (LP) separator 120. The pressure in the HP separator is maintained at 200–250 psig to minimize propylene and product losses, with excess gas being vented to the plant fuel gas system (not shown).

Liquid containing product and catalyst are then fed from the HP separator bottom through line 116 to the low pressure separator 120 where the pressure is controlled at about 80 psig. The overheads from LP separator 120 are cooled in exchanger 122, and condensed liquid is collected in tank 125. The offgas is vented via line 126 to the plant flare system (not shown), and the liquid from tank 125 is returned to the LP separator (arrow). Both the HP and LP flash drums provide additional residence time to complete reaction of olefin and syngas contained in the liquid stream prior to final product/catalyst separation.

From the LP separator, product flows via line 127 through a steam heater 128 to the product vaporizer 130. In the product vaporizer, the mixed aldehyde product is taken as an overhead vapor (arrow) to the heavies separator 140. The rhodium catalyst stream is taken from the bottom of the product vaporizer 130 (arrow), cooled and recycled to the oxonation reactor section. The temperature and pressure of the product vaporizer 130 are controlled to avoid the build-up of heavies (by-products) in the recycled catalyst stream, while minimizing temperatures to avoid catalyst degradation.

In the heavies separator 140, the heavies formed as a reaction by-product are taken as a bottoms stream (arrow) while the mixed aldehyde product is condensed from the overhead, for example, by passing the product through cooling water exchanger 143 and into condenser tank 145, and is then sent to tankage (not shown). A small product reflux stream is returned (arrow) to the top of the heavies separator 140 to effect the separation of the heavies stream from the product.

The heavies by-product stream from the bottom of 140 is sent via line 147 to the residue tank 150. This material contains product aldehyde and heavies and may contain trace amounts of ligand (tri-phenyl phosphine). Final disposition for this material is a batch distillation still (not shown) where product aldehyde and catalyst ligand are recovered and recycled to the heavies by-product purge stream (to maximize yields and minimize catalyst and chemical costs).

Finally, reactor temperature control is maintained through the use of a "closed-loop" tempered water cooling system. Heated tempered water is collected in the bottom of the product cooler 100-I and pumped (arrow) through the tempered water cooler 152 where heat is rejected to a central cooling water system. The cooled tempered water stream is then returned (arrow) and used for individual reactor bundle temperature control. The advantages of this system are two-fold. First, through the use of a "closed" system, the expensive catalyst may be contained and recovered in the event of a reactor tube leak. Second, the closed-loop provides excellent reactor temperature control in a regime necessary to ensure optimum catalyst life and activity, as well as maximum reaction selectivity to desired end products.

Figure 2:
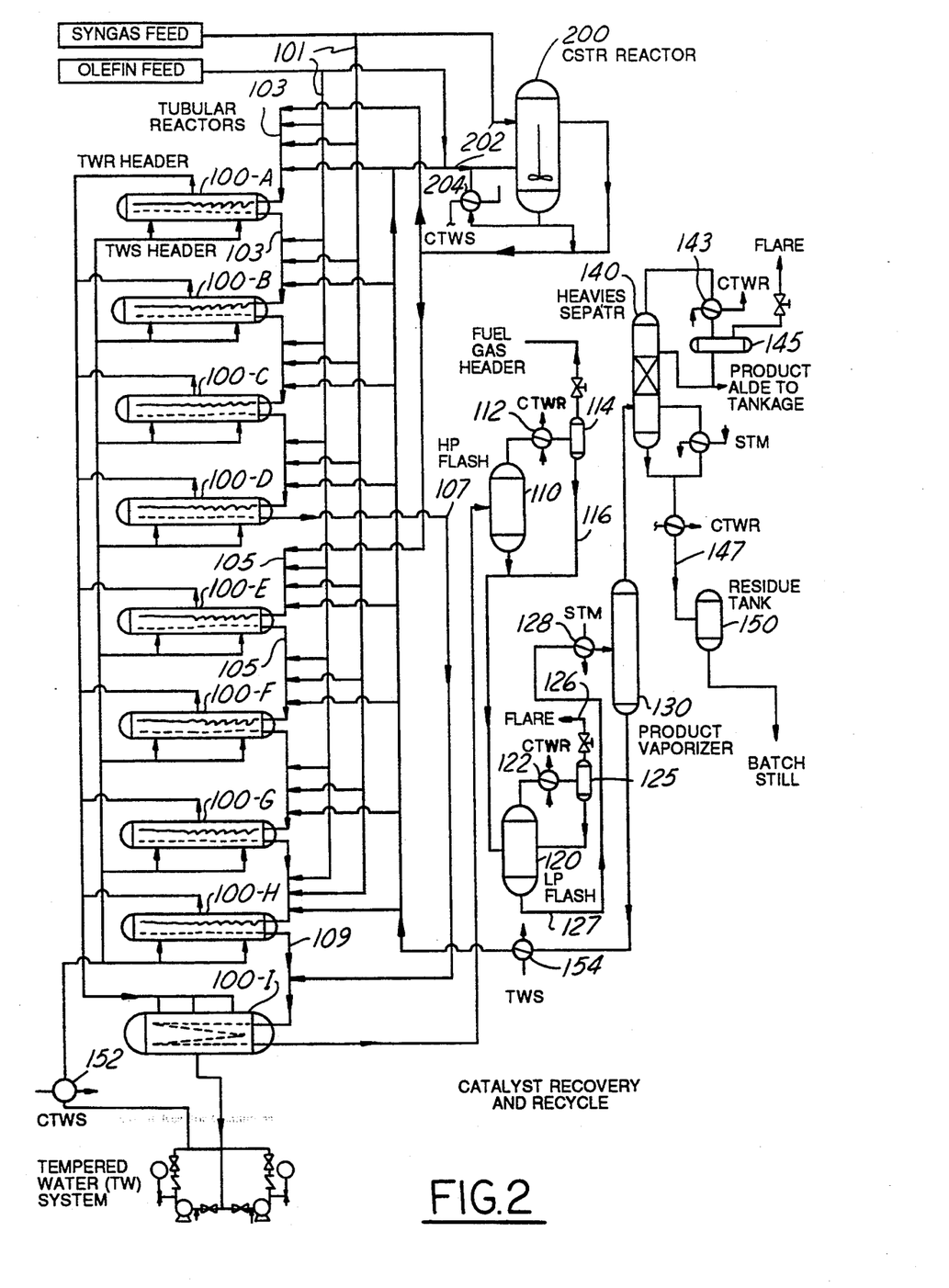
FIG. 2 is a schematic flow diagram of a system which employs a combination of the tubular reactor system and pot reactors.

FIG. 2 represents a detailed depiction of a combined tubular reactor/"CSTR" system. This system differs from that shown in FIG. 1 in that a continuous stirred tank reactor (CSTR) operates in the lead position, upstream of the tubular reactors. The use of the combined system greatly increases the production capacity of the available equipment while maintaining the yield/selectivity advantages of the "tubular" reactor system. (In FIGS. 1 and 2, like reference numerals indicate identical elements).

Olefin and syngas are fed through pre-treatment facilities (for the removal of potential reaction poisons) to the reactor feed manifold 202. Catalyst is recycled from the product vaporizer 130 through a cooler 154 to the reactor feed manifold 202. Catalyst, olefin and syngas feed are then injected into CSTR 200, which operates upstream of the tubular reactor bundles discussed hereinabove.

In the CSTR 200, partial hydroformylation of the olefin feed occurs according the chemistry described in U.S. Pat. No. 3,527,809, supra. The heat of reaction is removed through circulation (arrow) of the reaction fluid through an external cooler 204 back to the reactor. Liquid and vapor product from the pot (CSTR) reactor are combined and transferred as feed to the lead tubular reactors 100-A and 100-E. Additional catalyst, olefin and syngas feed are added to the pot reactor effluent, and reaction in the tubular reactors 100-A through 100-H occurs as described in the description of FIG. 1 above. Hydroformylation takes place in the tubular reactor according to the chemistry described in U.S. Pat. No. 3,527,809, supra.

Catalyst and product recovery also occur exactly as shown in FIG. 1 and described above. The primary advantage of this embodiment of the invention is that it makes use of existing equipment to enhance olefin yields and product selectivity at a minimum cost during the conversion of an existing "cobalt catalyzed" plant to "rhodium catalyst" technology. In previous conversions of similar plants, the "tubular reactors" were idled and discarded along with other related "cobalt catalyst" recovery facilities. Maximum olefin yields in the typical "rhodium" conversion were obtained by installing complex and expensive olefin recovery and recycle facilities. Through the re-use of existing equipment in a unique process as depicted in FIG. 2, acceptable olefin yields and product selectivity may be obtained at a fraction of the normal "technology conversion" cost.

Finally, the improved product selectivity obtained through enhanced tubular reactor control of olefin and syngas partial pressures, temperature and catalyst concentration would not be economical in a "grass roots" application as compared to other "typical" alternatives. The enhanced control becomes very competitive, however, when existing facilities are used during a technology conversion process. The abbreviations used in the figures are:
TWR—Tempered Water Return
TWS—Tempered Water Supply
CTWS—Cooling Tower Water Supply
CTWR—Cooling Tower Water Return
HP—High Pressure
LP—Low Pressure
CSTR—Constant Stirred Tank Reactor The invention is illustrated by the following non-limiting example.

Example

A computerized (calculated) study of a specific embodiment of the method of the invention was conducted as follows.

| Raw Materials | | |
|---|---|---|
| Propylene Purity: | Propane | 0.1 mole % |
| | Propylene | 99.9 mole % |
| Syngas Purity: | Hydrogen | 50.3 mole % |
| | CO | 49.7 mole % |

Utilizing the system of FIG. 2 in this study, propylene and syngas feeds are first introduced to the CSTR reactor 200 with reactor conditions as follows.

| CSTR Reactor Conditions | |
|---|---|
| Reaction Temperature | 100° C. |
| Reaction Pressure | 22.0 kg/cm$^2$ G |
| H$_2$/CO Feed Ratio | 1.01 |
| CO to Propene Feed Ratio | 0.95 mole/mole |
| Liquid Residence Time | about 1.5 hours |

| CSTR Reactor Conditions | |
|---|---|
| Rhodium Concentration | about 300 ppm |
| Triphenylphosphine Conc. | about 12% by weight |

About 90% of the total propylene reactant stream is fed to the CSTR, with the balance being fed to the tubular reactors as shown in FIG. 2. The CSTR reactor conditions are maintained to produce a >10:1 normal to iso-butyraldehyde product distribution.

Both liquid and vapor products from the CSTR reactor are combined, then split into equal streams feeding two parallel trains of tubular reactors, with conditions as follows.

| Tubular Reactor Conditions | |
|---|---|
| Reaction Temperature | 90–100° C. |
| Reaction Pressure | 17–20 kg/cm$^2$ G |
| H$_2$/CO Feed Ratio | 1.01 |
| CO to Propene Feed Ratio | 2.8 mole/mole |
| Liquid Residence Time | about 0.5 hours |
| Rhodium Concentration | about 300–350 ppm |
| Triphenylphosphine Conc. | about 12–14% by weight |

Effluent from the tubular reactor trains are again combined and cooled in product cooler 100-I to a temperature of about 85° C., then flashed in the high pressure separator 110. Pressure in the separator is calculated at about 17 kg/cm$^2$ with offgas cooling to about 42° C. Total propylene conversion across the oxonation section is calculated at >99%, with selectivity as follows.

| | |
|---|---|
| Conversion to n-butyraldehyde | about 90% |
| Conversion to i-butyraldehyde | about 9% |
| Conversion to by-products | about 1% |

Offgas from the HP separator is calculated to be approximately 5.5 wt. % of total feeds to the reactors (syngas and propylene) with the following composition.

| Vent Gas to Fuel | |
|---|---|
| Hydrogen | 56.4 mole % |
| CO | 41.3 mole % |
| Propane | <0.1 mole % |
| Propylene | <0.1 mole % |
| i-Butyraldehyde | 0.3 mole % |
| n-Butyraldehyde | 1.9 mole % |

Liquid effluent from the HP separator is pressured to the low pressure separator 120 where pressure is reduced to 6.3 kg/cm$^2$ and offgas is cooled to 43° C. prior to venting to flare. Total offgas from the LP separator was calculated at less than 0.5 wt. % of feed with a composition of 48 mole % CO, 47 mole % H$_2$ and 5 mole % n and i-butyraldehyde.

From the LP separator, effluent flows to the product vaporizer 130 where the stream is heated to 140° C. and flashed at 0.5 kg/cm$^2$ gage. Product is taken as an overhead stream from the vaporizer while catalyst is recycled from the bottom of 130 through a cooler back to oxonation. Vapor from the product vaporizer is fractionated in the heavies separator 140 to remove heavies (reaction by-products) from the mixed-aldehyde product stream. The bottoms product from the heavies separator (50% heavies, 50% butyraldehyde) is sent to tankage for further treatment/product recovery, for example, by use of a batch still. The overhead product from the tower is condensed and sent to tankage as a mixed aldehyde product stream with a calculated normal/iso ratio of 10:1. Non-condensables from the tower overhead are vented to the flare. A summary of the calculated reactor products/selectivity is shown below:

|  | Wt. % |
| --- | --- |
| Mixed Aldehyde Product | 9.29 |
| HP Separator Vent to Fuel | 5.5 |
| LP Separator Vent to Flare | 0.5 |
| Heavies Separator Vent to Flare | 0.3 |
| Heavies Separator Bottoms to Tankage | 0.8 |
| TOTAL | 100.0 |

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

What is claimed is:

1. In a process for the hydroformylation of olefins with carbon monoxide and hydrogen in the presence of a hydroformylation catalyst in a continuous tubular reactor, the improvement comprising:
   a. employing an olefin hydroformylation catalytically effective amount of a rhodium hydroformylation catalyst;
   b. maintaining the reaction temperature in said tubular reactor at less than about 145° C.; and
   c. maintaining the pressure within said tubular reactor at less than 450 psig and the partial pressure therein attributable to carbon monoxide no greater than about 90% of said total pressure;
   whereby said hydroformylated olefin product is rich in normal aldehydes.

2. The process of claim 1 wherein the ratio of rhodium catalyst to olefin is at least about $1 \times 10^{-6}$ mol of rhodium per mol of olefin.

3. The process of claim 1 wherein the ratio of rhodium catalyst to olefin is in the range of from about $1 \times 10^{-5}$ mol to about $1 \times 10^{-2}$ mol of rhodium per mol of olefin.

4. The process of claim 1 wherein the ratio of rhodium catalyst to olefin is in the range of from about $1 \times 10^{-4}$ mol to about $1 \times 10^{-2}$ mol of rhodium per mol of olefin.

5. The process of claim 1 wherein the pressure within said tubular reactor is maintained at less than about 350 psig.

6. The process of claim 1 wherein the pressure within said tubular reactor is maintained at between about 1 atm. and about 250 psig.

7. The process of claim 1 wherein the partial pressure in said tubular reactor attributable to carbon monoxide is in the range of from about 25% to about 90% of said total pressure.

8. The process of claim 1 wherein the partial pressure in said tubular reactor attributable to carbon monoxide is no greater than about 75% of said total pressure.

9. The process of claim 1 wherein the partial pressure in said tubular reactor attributable to carbon monoxide is in the range of from about 45% to about 75% of said total pressure.

10. The process of claim 1 wherein said reaction temperature is maintained at between about 50° C. and about 145° C.

11. The process of claim 1 wherein said reaction temperature is maintained at between about 60° C. and about 125° C.

12. The process of claim 1 wherein said reaction temperature is maintained at between about 65° C. and about 95° C.

13. The process of claim 1 wherein said rhodium hydroformylation catalyst comprises rhodium in complex combination with carbon monoxide and a ligand containing a trivalent atom of a Group VA element.

14. The process of claim 13 wherein said trivalent atom is phosphorous, arsenic or antimony.

15. The process of claim 13 wherein said ligand is a tertiary organo Group VA trivalent element.

16. The process of claim 13 wherein said ligand is a tertiary organo phosphorous, arsenic or antimony compound.

17. The process of claim 15 wherein each organo moiety is composed of (1) carbon and hydrogen atoms, or (2) carbon, hydrogen and aliphatic etheric oxygen atoms, each of said organo moieties being monovalently bonded to said trivalent Group VA element via a carbon atom or an aliphatic etheric oxygen atom thereof.

18. The process of claim 15 wherein said ligand is a trialkylphosphite, tricycloalkylphosphite, triarylphosphite or triarylphosphine.

19. The process of claim 1 wherein said hydroformylation takes place in the presence of a solvent for said carbon monoxide, hydrogen and catalyst.

20. The process of claim 19 wherein said solvent comprises recycled liquid reaction medium following at least partial hydroformylation of said olefins.

21. The process of claim 1 including the steps of substantially separating hydroformylated olefin product and catalyst from the reaction medium following said hydroformylation.

22. The process of claim 21 including the step of recycling said separated catalyst to said tubular reactor.

23. The process of claim 21 including the step of separating partially hydroformylated product and organic residue during said process and recycling either or both to said tubular reactor as solvent.

24. The process of claim 1 wherein said olefins, carbon monoxide and hydrogen are pre-mixed prior to entry into said tubular reactor.

25. The process of claim 24 wherein said pre-mixed olefins, carbon monoxide and hydrogen are fed into said reactor at multiple entry points along said tubular reactor.

26. The process of claim 24 wherein said hydroformylation catalyst is fed into said reactor at multiple entry points along said tubular reactor.

27. The process of claim 1 wherein, prior to said hydroformylation in said tubular reactor, said olefins are partially hydroformylated with carbon monoxide and hydrogen in the presence of a rhodium hydroformylation catalyst in at least one pot reactor.

28. The process of claim 27 wherein the mixture of olefins, carbon monoxide and hydrogen not consumed in the hydroformylation reaction occurring in said at least one pot reactor comprise the feed stock for said tubular reactor and is fed thereinto at multiple entry points therealong.

29. The process of claim 27 wherein multiple pot reactors connected in series are employed.

* * * * *

UNITED STATES PATENT AND TRADEMARK OFFICE
CERTIFICATE OF CORRECTION

PATENT NO. : 5,410,091
DATED : April 25, 1995
INVENTOR(S) : Charles S. Nall

It is certified that error appears in the above-indentified patent and that said Letters Patent is hereby corrected as shown below:

In Column 4, line 7, "AHNP" should read "ΔHNP"
In Column 4, line 13, "AHNP" should read "ΔHNP"
In Column 4, line 16, "AHNP" should read "ΔHNP"

Signed and Sealed this

Twenty-seventh Day of June, 1995

Attest:

BRUCE LEHMAN

*Attesting Officer*     *Commissioner of Patents and Trademarks*